United States Patent [19]
Suh et al.

[11] Patent Number: 5,962,658
[45] Date of Patent: Oct. 5, 1999

[54] (3-OXOISOINDOLIN-1-YLIDINE) PROPANDINITRILE DERIVATIVES AND METHOD FOR PREPARING THE SAME

[75] Inventors: Dong-Hack Suh, Daejeon; Hyun-Cheual Choi, Kwangju; Tae-Hyung Rhee, Sungnam, all of Rep. of Korea

[73] Assignee: SamSung Electronics Co., Ltd., Suwon, Rep. of Korea

[21] Appl. No.: 09/156,904

[22] Filed: Sep. 18, 1998

[30] Foreign Application Priority Data

Sep. 18, 1997 [KR] Rep. of Korea .................. 97-47600

[51] Int. Cl.$^6$ .................. C09B 29/036; C09B 29/09; C07D 209/44
[52] U.S. Cl. .................. 534/789; 548/472
[58] Field of Search .................. 534/789; 548/472

[56] References Cited

U.S. PATENT DOCUMENTS 5,602,074  2/1997  Klintz et al. .................. 548/472

OTHER PUBLICATIONS

Chem. Abs, 67: 73310& Chem. Ber. (1967), 100 (7), 2261–73, J. Krantz, "New Synthesis of 3–substituted Phthalimidines".
Dunn, A., "The Synthesis of Pyrrolopyridines and Pyridopyridazines", J. Heterocycl. Chem., 21(4), 965–8, 1984.
Kranz, J., Chemical Abstracts, 67:73310, 1967.

*Primary Examiner*—Fiona T. Powers
*Attorney, Agent, or Firm*—Robert E. Bushnell, Esq.

[57] ABSTRACT

Derivatives of (3-oxoisoindolin-1-ylidine)propandinitrile, and a method for preparing the derivatives, are disclosed herein. The (3-oxoisoindolin-1-ylidine)propandinitrile derivatives can be prepared easily and at low cost. Also, the derivatives show good heat resistance at temperatures required for manufacturing an electro-optic device, and can minimize light loss at a near infrared light wavelength range by replacing hydrogen of the C—H bond with halogen atom. As a result, the derivatives of the present invention are useful as an optical material for an electro-optic device. In addition, the (3-oxoisoindolin-1-ylidine)propandinitrile derivatives can be used as an intermediate for synthesizing a new compound having good electro-optic characteristics and heat resistance.

16 Claims, No Drawings

(3-OXOISOINDOLIN-1-YLIDINE) PROPANDINITRILE DERIVATIVES AND METHOD FOR PREPARING THE SAME

CLAIM OF PRIORITY

This application makes reference to, incorporates the same herein, and claims all benefits accruing under 35 U.S.C. §119 from an application for (3-OXOISOINDOLIN-1-YLIDINE) PROPANDINITRILE DERIVATIVES AND METHOD FOR PREPARING THE SAME earlier filed in the Korean Industrial Property Office on the 18$^{th}$ of Sep. 1997 and there duly assigned Ser. No. 47600/1997.

BACKGROUND OF THE INVENTION

1. Technical Field

The present invention relates to (3-oxoisoindolin-1-ylidine)propandinitrile derivatives as optically active chromophores and a method for preparing the derivatives.

2. Related Art

In a method for manufacturing an electro-optic device, an inorganic material, such as a semiconductor compound containing an element of group III–V in the periodic table, (e.g., LiNbO$_3$, InP or GaAs), is used. Such an electro-optic device employing the inorganic material has been introduced into the market.

Recently, research into a method for manufacturing an electro-optic device using an organic chromophore has been conducted, and such electro-optic device is partially commercialized.

An electro-optic characteristic of the inorganic material is derived from cleavage and recombination of bonds between molecules. Electro-optic characteristics of the organic chromophore originate from polarization of the π-electrons. Such an organic chromophore showing electro-optic characteristics based on the π-electron resonance structure has good optical characteristics, such as a non-linear optical characteristic, compared to those of an inorganic material. Also, because the organic chromophore is mostly synthesized, various characteristics including a mechanical characteristic and stability to heat, oxygen and light can be optimized. In addition, it is easily applied to a manufacturing process for an electro-optic device based on a semiconductor manufacturing process.

In manufacturing an electro-optic device, including an electro-optic integrated circuit (OEIC), an optical waveguide device and a multi-chip module (MCM) device, a general semiconductor manufacturing process is applied. Thus, an optical material used for manufacturing the electro-optic device should have thermal stability for a required time at a temperature required for manufacturing a semiconductor.

The thermal stability of the optical material is closely related to the glass transition temperature, the thermal decomposition temperature, the thermal expansion coefficient and birefrigency. Thus, it is preferable to select an optical material appropriate for the above characteristics, as well as thermal stability.

However, known organic chromophores are not sufficient to secure heat resistance at temperatures required in manufacturing an electro-optic device. That is, the organic chromophore decomposes at temperatures for manufacturing the electro-optic device.

In order to solve the above problem, research into a method for improving heat resistance of the organic chromophore has been conducted. However, improving the heat resistance of the chromophore deteriorates its electro-optic characteristics, and complicates synthesis of the chromophore.

In addition, known organic chromophores cause a light loss in the near infrared light wavelength range, which is used for optical communications. The large optical absorption loss in the near infrared light wavelength range is due to the organic chromophore absorbing light in the near infrared light wavelength range. In general, light absorption of the organic chromophore in the near infrared light wavelength range is caused by overtone of harmonics according to stretching and deformation vibrations of the carbon-hydrogen (C—H) bond in the organic chromophore. Thus, using the organic chromophore as an optical material for an optical waveguide necessarily results in considerable optical loss. In order to reduce such optical loss, the light absorption wavelength region of the organic chromophore should be shifted to a longer wavelength region or a shorter wavelength region. To this end, a method for replacing hydrogen (H) of the C—H bond with fluoride (F) or heavy hydrogen (D) has been suggested.

The method for replacing H with D is not suitable for a material for use in an optical communications device employing a wavelength of 1,500 nm because a C—D bond has large optical loss in a wavelength of 1,500 nm. On the other hand, the method for replacing H with F has been verified as a method which enables minimization of light absorption loss at a wavelength range of 1,000~1,700 nm.

SUMMARY OF THE INVENTION

To solve the above problems, it is an objective of the present invention to provide (3-oxoisoindolin-1-ylidine) propandinitrile derivatives which can minimize light absorption loss at a near infrared light wavelength range, which are very stable at temperatures for manufacturing an electro-optic device, and which are prepared easily.

It is another objective of the present invention to provide a method for preparing the (3-oxoisoindolin-1-ylidine) propandinitrile derivatives.

To achieve the first objective of the present invention, there are provided derivatives of (3-oxoisoindolin-1-ylidine) propandinitrile represented by the formula (1) as follows:

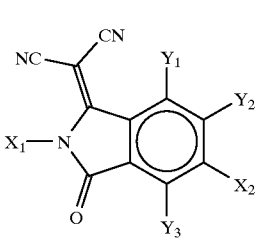

(1)

wherein $Y_1$, $Y_2$ and $Y_3$ are independently selected from the group consisting of hydrogen and halogen atom, $X_1$ is selected from the group consisting of hydrogen, halogen atom, —OR$_1$, —NHR$_1$, —COOR$_1$, —COR$_1$, —NO$_2$ and —N(R$_1$)(R$_2$) (where R$_1$ and R$_2$ are independently selected from the group consisting of hydrogen, C$_1$–C$_{20}$ unsubstituted or substituted aliphatic hydrocarbon, C$_5$–C$_{20}$ unsubstituted or substituted aliphatic cyclic hydrocarbon, and C$_6$–C$_{20}$ unsubstituted or substituted aromatic hydrocarbon); X$_2$ is selected from the group consisting of hydrogen, halogen atom, —OR$_1$, —NHR$_1$, —COOR$_1$, —COR$_1$, —NO$_2$ and —N(R$_1$)(R$_2$) (where R$_1$ and R$_2$ are independently selected from the group consisting of hydrogen, $C_1$–$C_{20}$ unsubstituted or substituted aliphatic hydrocarbon, $C_5$–$C_{20}$ unsubstituted or substituted aliphatic cyclic hydrocarbon, and $C_6$–$C_{20}$ unsubstituted or substituted aromatic hydrocarbon), and moieties represented by the following formulae:

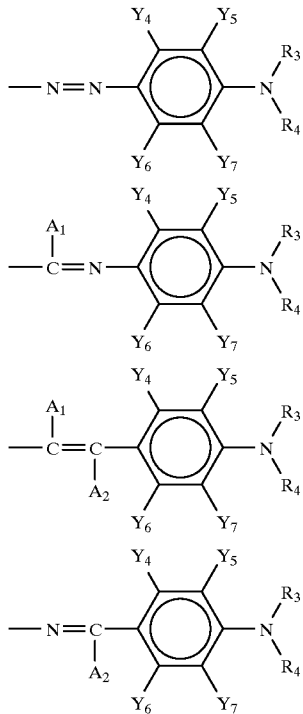

wherein $Y_4$, $Y_5$, $Y_6$ and $Y_7$ are independently selected from the group consisting of hydrogen and halogen atom; $A_1$ and $A_2$ are independently selected from the group consisting of $OR_5$ (where $R_5$ is hydrogen, alkyl or halogenated alkyl groups), H, F, Cl, Br and I; and $R_3$ and $R_4$ are independently selected from the group consisting of hydrogen, halogen atom, —$OR_1$, —$NHR_1$, —$COOR_1$, —$COR_1$, —$NO_2$ and —$N(R_1)(R_2)$ (where $R_1$ and $R_2$ are independently selected from the group consisting of hydrogen, $C_1$–$C_{20}$ unsubstituted or substituted aliphatic hydrocarbon, $C_5$–$C_{20}$ unsubstituted or substituted aliphatic cyclic hydrocarbon, and $C_6$–$C_{20}$ unsubstituted or substituted aromatic hydrocarbon).

Preferably, $X_2$ is selected from the moieties represented by the following formulae:

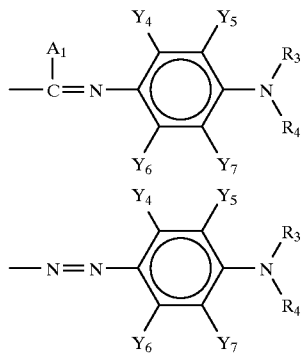
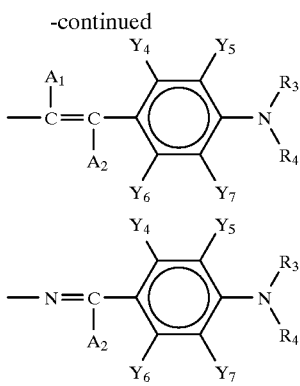

wherein $Y_4$, $Y_5$, $Y_6$ and $Y_7$ are independently selected from the group consisting of hydrogen and halogen atom; $A_1$ and $A_2$ are independently selected from the group consisting of $OR_5$ (where $R_5$ is hydrogen, alkyl or halogenated alkyl groups), H, F, Cl, Br and I; and $R_3$ and $R_4$ are independently selected from the group consisting of hydrogen, halogen atom, —$NHR_1$, —$OR_1$, —$COOR_1$, —$COR_1$, —$NO_2$, —$N(R_1)(R_2)$ (where $R_1$, and $R_2$ are independently selected from the group consisting of hydrogen, $C_1$–$C_{20}$ unsubstituted or substituted aliphatic hydrocarbon, $C_1$–$C_{20}$ unsubstituted or substituted aliphatic cyclic hydrocarbon, and $C_1$–$C_{20}$ unsubstituted or substituted aromatic hydrocarbon).

(3-Oxoisoindolin-1-ylidine)propandinitrile derivatives of formula (1) having $X_2$ represented by the following structure have good electro-optic characteristics due to a conjugated π-electron bond.

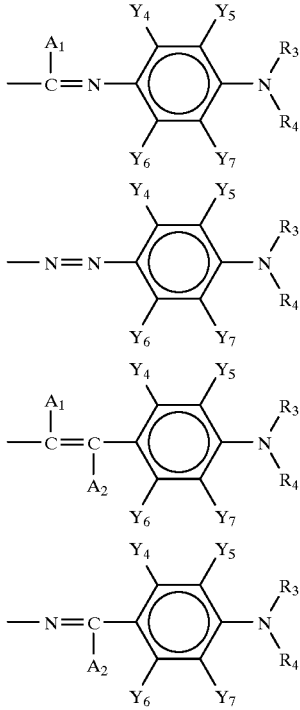

To achieve the second objective of the present invention, there is provided a method for preparing (3-oxoisoindolin-1-ylidine)propandinitrile derivatives represented by the formula (1), wherein a 1-imino-3-oxoisoindolin derivative represented by the formula (2) below and malononitrile ($NCCH_2CN$) were reacted at 0~200° C. for 0.5~96 hours:

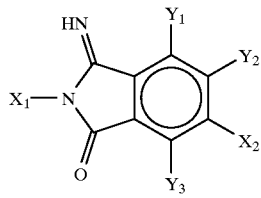

or

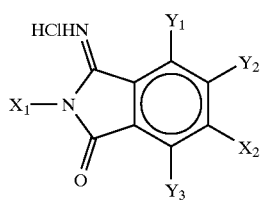

(2)

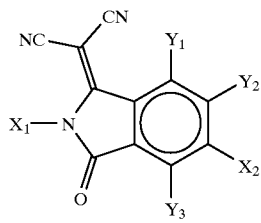

(1)

wherein $Y_1$, $Y_2$ and $Y_3$ are independently selected from the group consisting of hydrogen and halogen, $X_1$ is selected from the group consisting of hydrogen, halogen atom, —$NHR_1$, —$OR_1$, —$COOR_1$, —$COR_1$, —$NO_2$, —$N(R_1)(R_2)$ (where $R_1$ and $R_2$ are independently selected from the group consisting of hydrogen, $C_1$–$C_{20}$ unsubstituted or substituted aliphatic hydrocarbon, $C_1$–$C_{20}$ unsubstituted or substituted aliphatic cyclic hydrocarbon, and $C_1$–$C_{20}$ unsubstituted or substituted aromatic hydrocarbon); $X_2$ is selected from the group consisting of hydrogen, halogen, —$NR_1$, —$OR_1$, —$COOR_1$, —$COR_1$, —$NO_2$, —$N(R_1)(R_2)$ (where $R_1$ and $R_2$ are independently selected from the group consisting of hydrogen, $C_1$–$C_{20}$ unsubstituted or substituted aliphatic hydrocarbon, $C_1$–$C_{20}$ unsubstituted or substituted aliphatic cyclic hydrocarbon, and $C_1$–$C_{20}$ unsubstituted or substituted aromatic hydrocarbon), and moieties represented by the following formulae:

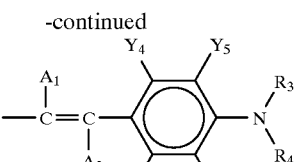

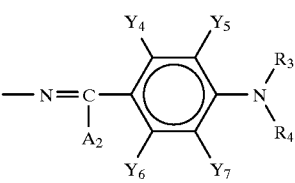

-continued

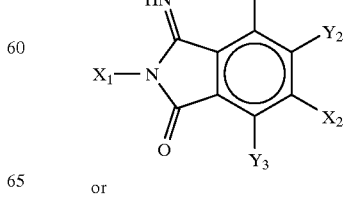

wherein $Y_4$, $Y_5$, $Y_6$ and $Y_7$ are independently selected from the group consisting of hydrogen and halogen atom; $A_1$ and $A_2$ are independently selected from the group consisting of $OR_5$ (where $R_5$ is hydrogen, alkyl or halogenated alkyl groups), H, F, Cl, Br and I; and $R_3$ and $R_4$ are independently selected from the group consisting of hydrogen, halogen atom, —$NR_1$, —$OR_1$, —$COOR_1$, —$COR_1$, —$NO_2$, —$N(R_1)(R_2)$ (where $R_1$ and $R_2$ are independently selected from the group consisting of hydrogen, $C_1$–$C_{20}$ unsubstituted or substituted aliphatic hydrocarbon, $C_1$–$C_{20}$ unsubstituted or substituted aliphatic cyclic hydrocarbon, and $C_1$–$C_{20}$ unsubstituted or substituted aromatic hydrocarbon).

DESCRIPTION OF THE PREFERRED EMBODIMENTS

Derivatives of (3-oxoisoindolin-1-ylidine)propandinitrile of the present invention have good thermal stability due to their imide functional groups. Also, because the derivatives have propandinitrile and an amide moieties as electron acceptors, electron accepting capacity thereof is good. In particular, if $X_2$ in the formula (1) is an electron acceptor, the (3-oxoisoindolin-1-ylidine)propandinitrile derivative has high polarity, which is appropriate for an optical material for an electro-optic device, as well as for an optical communications device requiring thermal stability.

Hereinafter, a method for preparing the (3-oxoisoindolin-1-ylidine)propandinitrile derivatives according to the present invention will be described.

1 mol of 1-imino-3-oxoisoindolin derivatives (Joachim Kranz, "New Synthesis of 3-Substituted Phthalimidines", Chem. Ber. 100(7), 2261–73 (1967)) represented by the formula (2) is added to a solvent, and 1~20 mol of malononitrile ($NCCH_2CN$) is added to the resultant and reacted at 0~200° C. for 0.5~96 hours. Here, the reaction end point is when the color of the reaction solution changes into a reddish yellow color.

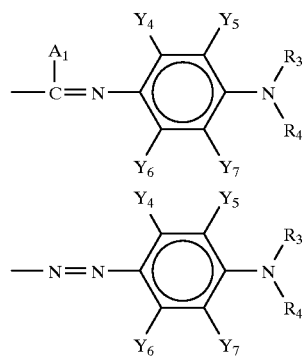

or

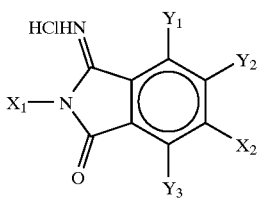

(2)

After the reaction is completed, the reaction mixture is cooled, resulting in precipitate of a deep reddish yellow color.

The precipitate is recrystalized to obtain (3-oxoisoindolin-1-ylidine)propandinitrile derivatives represented by the formula (1).

Hereinafter, the present invention will be described in detail through the following examples. However, the present invention is not limited to the following examples.

EXAMPLE 1

A mixture containing 0.01 mol (1.91 g) of 1-imino-3-oxo-5-nitroisoindoline, 0.01 mol (6.6 g) of malononitrile and 50 ml of isopropylalcohol was refluxed with stirring. The reaction was terminated when the color of the reaction mixture changed into a reddish yellow color.

The reaction mixture was cooled to room temperature, resulting in a precipitate. The precipitate was filtered and purified. The resultant was dried in a vacuum oven set to 30° C. for 24 hours, resulting in (3-oxo-5-nitroisoindolin-1-ylidine)propandinitrile (yield: 70%).

EXAMPLE 2

0.01 mol (2.4 g) of the (3-oxo-5-nitroisoindolin-1-ylidine) propandinitrile obtained by Example 1, and 0.3 g of palladium (Pd) on activated carbon (Pd content: 10%) were added to 80 ml of dimethylsulfoxide, and then the resultant was mixed. The mixture was hydrogenated at 80° C. and 60 psi for 24 hours.

The reaction mixture was cooled to room temperature, and then water was added to the mixture. The precipitate was filtered and purified. The resultant was dried at a vacuum oven set to 100° C. for 24 hours, resulting in (3-oxo-5-aminoisoindolin-1-ylidine)propandinitrile (yield: 80%).

EXAMPLE 3

0.01 mol (2.1 g) of the (3-oxo-5-aminoisoindolin-1-ylidine)propandinitrile obtained by Example 2, 0.28 g of sodium nitrate and 4.0 ml of 35% HCl were mixed with 40 ml of water, and the mixture was stirred for 30 minutes.

After dropwisely adding N-phenyldiethanolamine (0.01 mol, 0.91 g) dissolved in 40 ml of ethanol to the reaction mixture for 30 minutes, the mixture was reacted for 2 hours.

After the reaction was completed, the obtained precipitate was filtered and purified. The resultant was dried in a vacuum oven set to 30° C. for 24 hours, resulting in {3-oxo-5-[4-(N,N-hydroxyethyl)phenyldiazo]isoindolin-1-ylidine)}propandinitrile (yield: 80%).

EXAMPLE 4

A mixture containing 0.1 mol (1.91 g) of 1-imino-3-oxo-5-nitroisoindoline, 0.11 mol (7.3 g) of malononitrile and 150 ml of methylglycolmonoethylether was stirred at 140° C. for 3 hours. The reaction was contined until the color of the reaction mixture changed to a reddish yellow color.

After cooling the reaction mixture to room temperature, the obtained precipitate was filtered and purified. The resultant was dried in a vacuum oven set to 30° C. for 24 hours, resulting in (3-oxo-5-nitroisoindolin-1-ylidine) propandinitrile (yield: 70%).

EXAMPLE 5

0.01 mol (2.4 g) of (3-oxo-5-nitroisoindolin-1-ylidine) propandinitrile obtained by Example 4 and 0.012 mol (5.7 g) of p-tolylleadtriacetate were added to 85 ml of dichloromethane and 15 ml of N,N-dimethylformamide, and the resultant mixture was reacted at 70° C. for 3 hours.

After the reaction was completed, the obtained precipitate was purified. The resultant was dried in a vacuum oven set to 80° C. for 24 hours, resulting in (3-oxo-5-nitro-N-tolylisoindolin-1-ylidine)propandinitrile (yield: 80%).

EXAMPLE 6

0.01 mol (3.3 g) of (3-oxo-5-nitro-N-tolylisoindolin-1-ylidine)propandinitrile obtained by Example 5 and 0.3 g of Pd on activated carbon (Pd content: 10%) were added to 80 ml of methanol. The resultant mixture was hydrogenated at 40° C. and 60 psi for approximately 12 hours.

After cooling the reaction mixture to room temperature, water was added to the mixture to form precipitate. The precipitate was filtered, purified, and then dried at a vacuum oven set to 30° C. for 2 hours, resulting in (3-oxo-6-amino-N-tolylisoindolin-1-ylidine)propandinitrile (yield: 85%).

EXAMPLE 7

A mixture of 0.1 mol (29.4 g) of 1-imino-3-oxo-5-nitro-4,6,7-trichloroisoindoline, 0.11 mol (7.3 g) of malononitrile and 150 ml of methylglycolmonomethylether were reacted at 150° C. for 3 hours with stirring.

The reaction mixture was added to a mixture containing methanol and water in a volume ratio of 1:1 to form a precipitate. The precipitate was filtered and purified, and dried in a vacuum oven set to 50° C., resulting in (3-oxo-5-nitro-4,6,7-trichloroisoindolin-1-ylidine)propandinitrile (yield: 80%).

EXAMPLE 8

0.01 mol (3.43 g) of(3-oxo-5-nitro-4,6,7-trichloroisoindolin-1-ylidine)propandinitrile, obtained by Example 7, and 0.3 g of Pd on activated carbon (Pd content: 10%) were added to 80 ml of methanol. The mixture was hydrogenated at 40° C. and 60 psi for approximately 25 hours.

The reaction mixture was cooled to room temperature, and water was added to the mixture to form a precipitate. The precipitate was filtered and purified, and dried in a vacuum oven set to 30° C. for 24 hours, resulting in (3-oxo-5-amino-4,6,7-trichloroisoindolin-1-ylidine) propandinitrile (yield: 80%).

EXAMPLE 9

0.01 mol (3.14 g) of (3-oxo-5-amino-4,6,7-trichloroisoindolin-1-ylidine)propandinitrile, obtained by Example 8, 0.28 g of sodium nitrate and 8.0 ml of 35% HCl were added to 120 ml of water, and mixed for 1 hour.

N-phenyldiethanolamine (0.01 mol, 0.91 g) dissolved in 40 ml of ethanol was added dropwisely to the mixture for 30 minutes, and reacted for 3 hours.

After the reaction was completed, the precipitate was filtered and purified. The resultant was dried in a vacuum oven set to 30° C. for 24 hours, resulting in {3-oxo-5-[4-(N,N-hydroxyethyl)phenyldiazo]-4,6,7-trichloroisoindolin-1-ylidine}propandinitrile (yield: 80%).

The organic chromophores obtained by implementing Examples 1 through 9 were comparatively easy to prepare, unlike a general heterocycle organic chromophore.

Also, heat resistance and light absorption loss at a near infrared light wavelength range of 1,000~1,700 nm were measured for the organic chromophores obtained by Examples 1 through 9.

As a result, the heat resistance of the organic chromophores obtained by Examples 1 through 9 was good, and the light absorption loss thereof was very small.

The (3-oxoisoindolin-1-ylidine)propandinitrile derivatives according to the present invention can be prepared easily and cheaply. Also, the derivatives show good heat resistance at a temperature required for manufacturing an electro-optic device, and can minimize light loss at a near infrared light wavelength range by substituting hydrogen of C—H bond for halogen atom. As a result, the derivatives of the present invention as useful as an optical material for an electro-optic device.

In addition, the (3-oxoisoindolin-1-ylidine) propandinitrile derivatives according to the present invention can be used as an intermediate for synthesizing a new compound having good electro-optic characteristics and heat resistance.

It should be understood that the present invention is not limited to the particular embodiment disclosed herein as the best mode contemplated for carrying out the present invention, but rather that the present invention is not limited to the specific embodiments described in this specification except as defined in the appended claims.

What is claimed is:

1. A compound represented by the formula

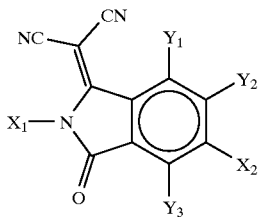

where $Y_1$, $Y_2$ and $Y_3$ are each independently selected from the group consisting of hydrogen and halogen;

where $X_1$ is selected from the group consisting of hydrogen, halogen, $-NHR_1$, $-OR_1$, $-COOR_1$, $-COR_1$, $-NO_2$, and $-N(R_1)(R_2)$, where $R_1$ and $R_2$ are independently selected from the group consisting of hydrogen, $C_1-C_{20}$ unsubstituted or substituted aliphatic hydrocarbon, $C_1-C_{20}$ unsubstituted or substituted aliphatic cyclic hydrocarbon, and $C_1-C_{20}$ unsubstituted or substituted aromatic hydrocarbon; and where $X_2$ is selected from the group consisting of hydrogen, halogen, $-NHR_1$, $-OR_1$, $-COOR_1$, $-COR_1$, $-NO_2$, $-N(R_1)(R_2)$ and moieties represented by the following formulae:

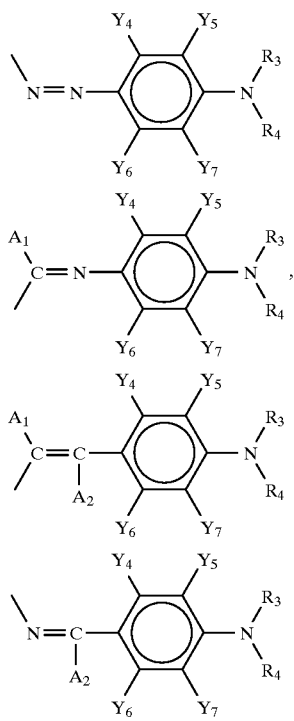

where $R_1$ and $R_2$ are independently selected from the group consisting of hydrogen, $C_1-C_{20}$ unsubstituted or substituted aliphatic hydrocarbon, $C_1-C_{20}$ unsubstituted or substituted aliphatic cyclic hydrocarbon, and $C_1-C_{20}$ unsubstituted or substituted aromatic hydrocarbon; $Y_4$, $Y_5$, $Y_6$ and $Y_7$ are independently selected from the group consisting of hydrogen and halogen atom; $A_1$ and $A_2$ are independetly selected from the group consisting of $OR_5$ (where $R_5$ is a hydrogen, alkyl or halogenated alkyl group), H, F, Cl, Br and I; and $R_3$ and $R_4$ are independently selected from the group consisting of hydrogen, halogen atom, $-NHR_1$, $-OR_1$, $-COOR_1$, $-COR_1$, $-NO_2$, and $-N(R_1)(R_2)$; and where $X_1$, $X_2$, $Y_1$, $Y_2$ and $Y_3$ are not all hydrogen.

2. The compound of claim 1, where $X_2$ is hydrogen, and where at least one of $Y_1$, $Y_2$ and $Y_3$ is halogen.

3. The compound of claim 1, where $X_2$ is hydrogen, and where $X_1$ is selected from the group consisting of halogen, $-NHR_1$, $-OR_1$, $-COOR_1$, $-COR_1$, $-N(R_1)(R_2)$, where $R_1$ and $R_2$ are independently selected from the group consisting of hydrogen, $C_1-C_{20}$ unsubstituted or substituted aliphatic hydrocarbon, $C_1-C_{20}$ unsubstituted or substituted aliphatic cyclic hydrocarbon, and $C_1-C_{20}$ unsubstituted or substituted aromatic hydrocarbon.

4. The compound of claim 1, where $X_3$ is selected from the group consisting of the moieties represented by the following formulae:

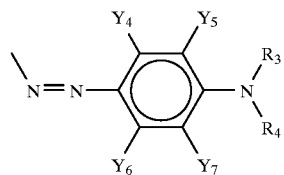

-continued

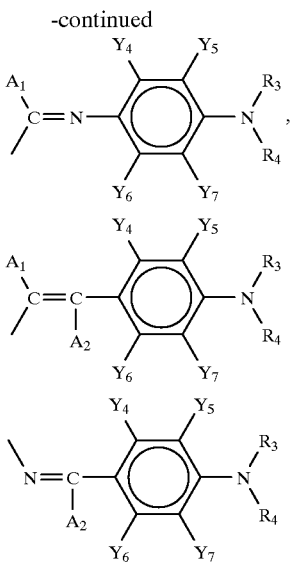

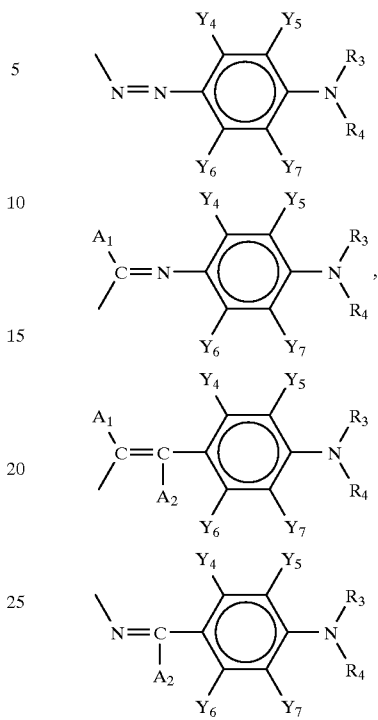

where $Y_4$, $Y_5$, $Y_6$ and $Y_7$ are independently selected from the group consisting of hydrogen and halogen atom; $A_1$ and $A_2$ are independently selected from the group consisting of $OR_5$ (where $R_5$ is a hydrogen, alkyl or halogenated alkyl group), H, F, Cl, Br and I; and $R_3$ and $R_4$ are indepedently selected from the group consisting of hydrogen, halogen atom, —$NHR_1$, —$OR_1$, —$COOR_1$, —$COR_1$, —$NO_2$, and —$N(R_1)(R_2)$, where $R_1$ and $R_2$ are independently selected from the group consisting of hydrogen, $C_1$–$C_{20}$ unsubstituted or substituted aliphatic hydrocarbon $C_1$–$C_{20}$ unsubstituted or substituted aliphatic cyclic hydrocarbon, and $C_1$–$C_2$ unsubstituted or substituted aromatic hydrocarbon.

5. A method for preparing a (3-oxoisoindolin-1-ylidine) propandinitrile derivative, comprising the steps of:

mixing a 1-imino-3-oxoisoindolin derivative, malononitrile, and a solvent; and allowing the mixture to react at a temperature in the range of approximately 0 to 200° C. for a time in the range of approximately 0.5 to 96 hours;

said 1-imino-3-oxoisoindolin derivative being

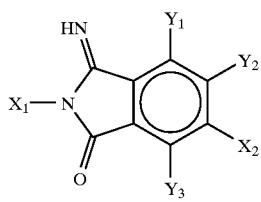

where $Y_1$, $Y_2$ and $Y_3$ are each independently selected from the group consisting of hydrogen and halogen;

where $X_1$ is selected from the group consisting of hydrogen, halogen, —$NHR_1$, —$OR_1$, —$COOR_1$, —$COR_1$, —$NO_2$, and —$N(R_1)(R_2)$, where $R_1$ and $R_2$ are independently selected from the group consisting of hydrogen, $C_1$–$C_{20}$ unsubstituted or substituted aliphatic hydrocarbon, $C_1$–$C_{20}$ unsubstituted or substituted aliphatic cyclic hydrocarbon, and $C_1$–$C_2$, unsubstituted or substituted aromatic hydrocarbon; and where $X_2$ is selected from the group consisting of hydrogen, halogen, —$NHR_1$, —$OR_1$, —$COOR_1$, —$COR_1$, —$NO_2$, —$N(R_1)(R_2)$ and moieties represented by the following formulae:

where $R_1$ and $R_2$ are independently selected from the group consisting of hydrogen, $C_1$–$C_{20}$ unsubstituted or substituted aliphatic hydrocarbon, $C_1$–$C_{20}$ unsubstituted or substituted aliphatic cyclic hydrocarbon, and $C_1$–$C_2$ unsubstituted or substituted aromatic hydrocarbon; $Y_4$, $Y_5$, $Y_6$ and $Y_7$ are independently selected from the group consisting of hydrogen and halogen atom; $A_1$ and $A_2$ are independently selected from the group consisting of $OR_5$ (where $R_5$ is a hydrogen, alkyl or halogenated alkyl group), H, F, Cl, Br and I; and $R_3$ and $R_4$ are independently selected from the group consisting of hydrogen, halogen atom, —$NHR_1$, —$OR_1$, —$COOR_1$, —$COR_1$, —$NO_2$, and —$N(R_1)(R_2)$, and where $X_1$, $X_2$, $Y_1$, $Y_2$, and $Y_3$ are not all hydrogen.

6. The method of claim 5, further comprising:
in said mixing step, using a mole ratio of the malononitrile to the 1-imino-3-oxoisoindolin derivative in the range of approximately 1 to 20.

7. The method of claim 5, further comprising the step of stopping the reaction when the reaction mixture changes to a reddish yellow color.

8. The method of claim 7, said step of stopping the reaction comprising cooling the reaction mixture.

9. The method of claim 8, further comprising the step of isolating a precipitate formed upon cooling the reaction mixture.

10. The method of claim 9, further comprising the step of recrystallizing the obtained precipitate to obtain the (3-oxoisoindolin-1-ylidine)propandinitrile derivative.

11. The method of claim 6, further comprising the step of stopping the reaction when the reaction mixture changes to a reddish yellow color.

12. The method of claim 11, said step of stopping the reaction comprising cooling the reaction mixture.

13. The method of claim 12, further comprising the step of isolating a precipitate formed upon cooling the reaction mixture.

14. The method of claim 13, further comprising the step of recrystallizing the obtained precipitate to obtain the (3-oxoisoindolin-1-ylidine)propandinitrile derivative.

15. The method of claim 5, said solvent being isopropylalcohol or metylglycolmonoethylether.

16. The method of claim 7, further comprising the step of adding the reaction mixture to a mixture of methanol and water to form a precipitate.

* * * * *

UNITED STATES PATENT AND TRADEMARK OFFICE
CERTIFICATE OF CORRECTION

PATENT NO. : 5,962,658
DATED : October 5, 1999
INVENTOR(S) : Dong-Hack Suh et al.

It is certified that error appears in the above-identified patent and that said Letters Patent is hereby corrected as shown below:

<u>Title page,</u>
Item [73], Assignee, enter the second Assignee's name -- Korea Research Institute of Chemical Technology. --

Signed and Sealed this

Fifth Day of August, 2003

JAMES E. ROGAN
*Director of the United States Patent and Trademark Office*